United States Patent [19]

Buckler et al.

[11] 4,109,001

[45] Aug. 22, 1978

[54] ARYL-SUBSTITUTED TRIAZOLYL PROPIONIC ACIDS

[75] Inventors: Robert Thomas Buckler, Edwardsburg, Mich.; Elva Kurchacova, Elkhart, Ind.

[73] Assignee: Miles Laboratories, Inc., Elkhart, Ind.

[21] Appl. No.: 840,523

[22] Filed: Oct. 11, 1977

Related U.S. Application Data

[63] Continuation-in-part of Ser. No. 763,504, Jan. 28, 1977, abandoned, which is a continuation-in-part of Ser. No. 706,065, Jul. 16, 1976, abandoned.

[51] Int. Cl.² .................... C07D 249/08; A61K 31/41
[52] U.S. Cl. ..................................... 424/269; 544/132; 260/308 R
[58] Field of Search ...................... 260/308 R; 424/269

[56] References Cited

U.S. PATENT DOCUMENTS

| | | |
|---|---|---|
| 3,681,374 | 8/1972 | Yano et al. ........................ 260/308 R |
| 3,769,411 | 10/1973 | Seidel et al. ...................... 260/308 R |
| 3,879,404 | 4/1975 | Baldwin et al. ................ 260/294.8 F |

*Primary Examiner*—Alton D. Rollins
*Attorney, Agent, or Firm*—J. D. McNeil

[57] ABSTRACT

Aryl-substituted-1,2,4-triazolyl propionic acid compounds, possessing antiinflammatory activity are disclosed. The compounds include: 3-[3-phenyl-1,2,4,(1H)-triazol-5-yl] propionic acid monohydrate; 3-[1-(3-chloro) phenyl and 3-[1-(3,5-dichloro)-phenyl-1,2,4,(1H)-triazol-3-yl] propionic acid; 3-[3-phenyl, 3-[3-(3-bromo)phenyl, 3-[3-(3-chloro)phenyl, and 3-[3-(4-methyl)-phenyl-1,2,4,(1H)-triazol-1-yl] propionic acid.

12 Claims, No Drawings

ARYL-SUBSTITUTED TRIAZOLYL PROPIONIC ACIDS

REFERENCE TO PRIOR APPLICATION

This is a continuation-in-part of U.S. Patent application Ser. No. 763,504, filed on Jan. 28, 1977, now abandoned which in turn was a continuation-in-part of U.S. Patent application Ser. No. 706,065, filed on July 16, 1976, now abandoned.

DESCRIPTION OF THE PRIOR ART

U.S. Pat. No. 3,900,492 discloses phenyl-1,2,3-triazolyl and (substituted)-phenyl-1,2,3-triazolyl alkanoic and alkanoic acids. U.S. Pat. No. 3,879,404 discloses 5-(pyridyl)-3-(phenyl)-1,2,4-triazoles, and U.S. Pat. No. 3,882,134 discloses 1-substituted-3,5-dipyridyl-1,2,4,-triazoles.

SUMMARY OF THE INVENTION

The instant invention is directed to 1,2,4-triazolyl propionic acids and pharmacologically acceptable, non-toxic salts thereof, which can be conveniently represented by the following three subclasses:

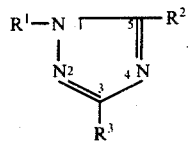

I 3-aryl-1,2,4,(1H)-triazol-5-yl propionic acid

In formula I, $R^1$, $R^2$ and $R^3$ are always dissimilar,
$R^1$ is hydrogen, $R^2$ is 2-carboxyethyl, and
$R^3$ is phenyl.

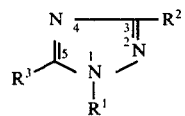

II 1-aryl-1,2,4,(1H)-triazol-3-yl-propionic acid

In Formula II, $R^1$, $R^2$ and $R^3$ are always dissimilar,
$R^1$ is mono-chlorophenyl or di-chlorophenyl;
$R^2$ is 2-carboxyethyl; and
$R^3$ is hydrogen.

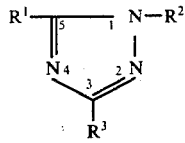

III 3-aryl-1,2,4,(1)-triazol-1-yl-propionic acid

In Formula III, $R^1$, $R^2$ and $R^3$ are always dissimilar,
$R^1$ is hydrogen, $R^2$ is 2-carboxyethyl, and
$R^3$ is phenyl, 4-methylphenyl, mono-bromophenyl and monochlorophenyl.

DESCRIPTION OF THE INVENTION

The following compounds comprise embodiments of the invention:
1. 3-[3-phenyl-1,2,4,(1H)-triazol-5-yl]propionic acid monohydrate;
2. 3-[1-(3-chloro)-phenyl-1,2,4,(1H)-triazol-3-yl]propionic acid;
3. 3-[1-(3,5-dichloro)-phenyl-1,2,4,(1H)-triazol-3-yl]-propionic acid;
4. 3-[3-phenyl-1,2,4,(1H)-triazol-1-yl]propionic acid;
5. 3-[3-(3-bromo)-phenyl-1,2,4,(1H)-triazol-1-yl]propionic acid;
6. 3-[3-(3-chloro)-phenyl-1,2,4,(1H)-triazol-1-yl]propionic acid;
7. 3-[3-(4-methyl)-phenyl-1,2,4,(1H)-triazol-1-yl]propionic acid.

A correlation between the embodiments listed heretofor and Formulas I, II and III is shown below.

TABLE I

| COMPOUNDS | FORMULA |
|---|---|
| 1 | Class I |
| 2 and 3 | Class II |
| 4 through 7 | Class III |

In general, the compounds of the invention are prepared as described below.

The 3-aryl-1,2,4,(1H)-traizol-5-yl-propionic acids of class I are made by warming together an ethyl arylimino ether and a ω-hydroxypropionic acid hydrazide to form an acylated amidrazone [See *J. Gen. Chem., U.S.S.R.* 29, 2105 (1959)]:

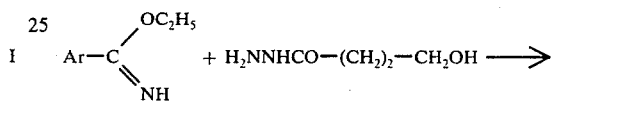

A      B

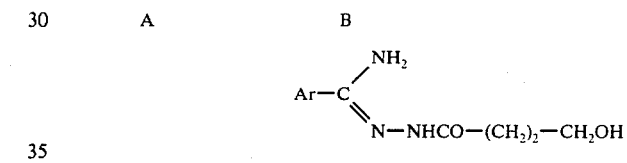

C

The acylated amidrazone C is heated to form a triazole by cyclization:

C

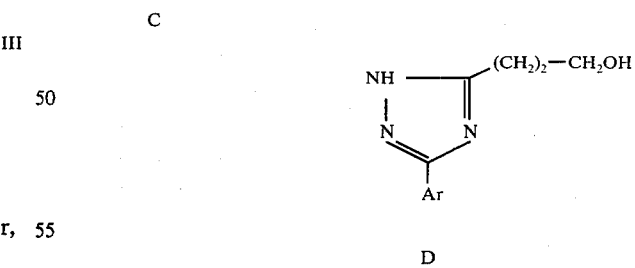

D

Oxidation of the triazole D at about 5° to 10° C in the presence of a chromium trioxide-acetic acid yields the desired triazolyl propionic acid. Optionally, the imino ether and ω-hydroxypropionic acid hydrazide can be stirred together at room temperature for about seven days, heated on a wood's metal bath and oxidized with chromium trioxide-acetic acid.

The 1-aryl-1,2,4,(1H)-triazol-3-yl propionic acids of class II are prepared from 1-(1-aryl-1,2,4,(1H)-triazol-3-yl) acetones by the modified Willgerodt reaction illustrated below to produce a thiomorpholid [See *Organic*

Reactions, Vol. III, p. 83 (1946)]. The acetone starting materials can be made by heating formamidines in ethanolic sodium ethoxide as described in *Tetrahedron* 20, 159 (1964).

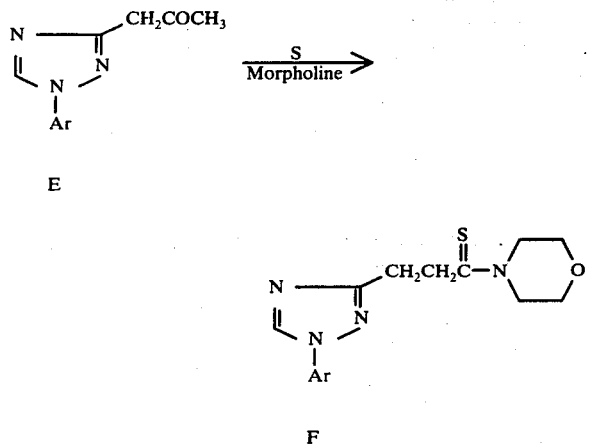

E

F

The thiomorpholid shown in F is hydrolyzed to yield the desired triazolyl propionic acid;

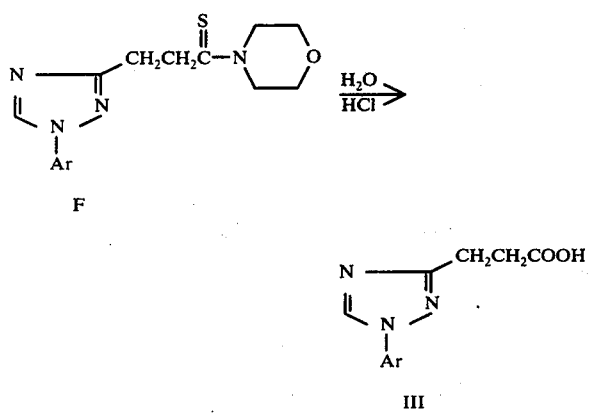

F

III

The 3-aryl-1,2,4,(1H)-triazolyl-propionic acids of class III are prepared by a synthesis route similar to that described previously for class I triazolyl propionic acids. The starting material G is prepared by mixing together at room temperature, in ethanol, a substituted ethyl aryl-imino ether with formyl hydrazine to yield a 3-aryl triazole:

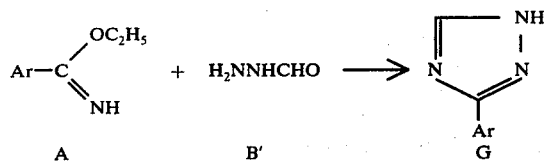

A B' G

Alkylation of the 3-aryl triazole with the appropriate ω-halopropionic acid by mixing together and refluxing the triazole and acid yields the desired triazolyl acid;

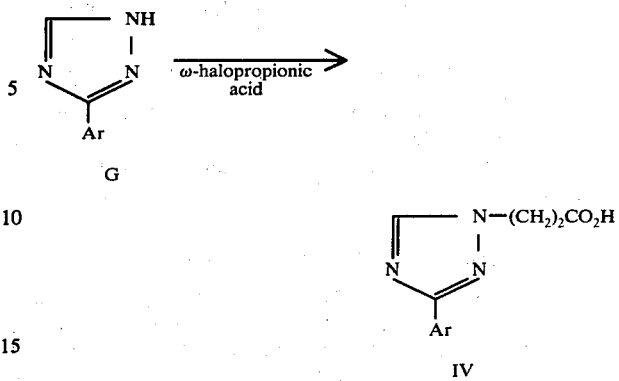

G

IV

The aryl-substituted 1,2,4-triazolyl propionic acids represented by Class I, II and III structural formulas possess antiinflammatory activity.

The compounds of the present invention are useful in treating algia by producing analgesic effect, i.e., reduction of pain, in an individual, for whom such therapy is indicated. The analgesic effect is produced by administering to that individual an effective analgesic amount of a compound having the structure indicated as formula I. The term "individual" as utilized in this specification means a human being or an experimental animal that is a model for a human being. "Therapeutically effective amount" means a dosage or a series of dosages that is effective in producing an analgesic effect in an individual in whom it is indicated. Medical indications for the use of the analgesics of the present invention are any conditions in which it is desired to treat algia in an individual. Although the amount will vary from individual to individual and from indication to indication it is easily determined by one skilled in the art without undue experimentation. Dose forms for the administration of the analgesic can be prepared by recognized methods in the pharmaceutical sciences.

The antiinflammatory activity was determined in the rat pleural effusion model of inflammation (as described in *Proc. Soc. Exptl. Biol. Med.*, 127, 597 (1968) and/or in the adjuvant arthritis model of inflammation (a modification of the method of Walz, et al., *J Pharmacol. Exptl. Therap.*, 178, 223 (1971).

The rat pleural effusion test involved producing an inflammation which results in a volume increase of pleural fluid. The inhibition of volume increase by the administration of the triazolyl propionic acids was then measured. The rat adjuvant arthritis test involved inducing chronic arthritis in the hind feet of rats and administering the triazolyl propionic acids. The change in foot edema volume for both the injected and uninjected foot was then determined.

The antiinflammatory activity of the compounds of the invention is listed in Table II as the activity of the reference drug (R) phenylbutazone, to that of the compound tested (E). The compound numbers refer to the embodiments previously described. The symbols AA and PE refer to adjuvant arthritis and pleural effusion models of inflammation, respectively.

TABLE II

| Compound | R/E* | |
|---|---|---|
| | AA | PE |
| Class I | | |
| 1 | 6.60 | >10.0 |
| Class II | | |

TABLE II-continued

| Compound | R/E* AA | PE |
|---|---|---|
| 2 | — | 5.99 |
| 3 | 0.95 | 8.91 |
| Class III | | |
| 4 | 4.89 | >10.0 |
| 5 | >10.0 | 5.16 |
| 6 | 6.00 | 2.96 |
| 7 | >10.0 | 7.40 |

*Percent reduction from control; phenylbutazone ÷ test compound

Inflammation of tissue is accompanied by swelling, and therefore compounds which exhibit antiinflammatory effects can be measured by measuring the reduction in tissue swelling, as indicated by change in size (volume) of the tissue, or the reduction in the amount of fluid exudate from increased capillary permeability, attributed to the test compound.

Because the mechanism by which antiinflammatory compounds operate is not fully understood, laboratory tests on animals often involve more than one test to measure the properties of the compounds being tested. One skilled in the art recognizes that demonstration of activity in at least one animal model of inflammation indicates that the compound is effective as an antiinflammatory compound.

The test results listed above summarize the measurement of decrease in pleural fluid volume and in foot edema volume discussed above. All of the triazolyl propionic acids listed above exhibited antiinflammatory activity in at least one model of inflammation.

The results of studies of the structural-activity relationship of the triazolyl propionic acids appear to indicate that the antiinflammatory activity is somehow influenced by the arrangement of the hetero atoms on the five-membered ring. The presence or absence of substituents on the aryl-substituent may also influence the antiinflammatory activity.

DESCRIPTION OF THE PREFERRED EMBODIMENTS

The product of Example 1 has the structure shown in Formula I wherein $R^1$ is hydrogen, $R^2$ is 2-carboxyethyl and $R^3$ is phenyl:

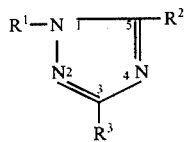

EXAMPLE 1

3-[3-phenyl-1,2,4,(1H)-triazol-5-yl]propionic acid monohydrate

A solution of 37 g (0.2 mole) of ethyl benzimino ether in 400 ml of warm absolute ethanol was neutralized with a solution prepared by dissolving 4.6 g (0.2 g/atom) of sodium in 300 ml absolute ethanol. The precipitate of NaCl was removed and a 23.6 g (0.2 mole) portion of finely ground 4-hydroxybutyrohydrazide was added [See J. Am. Chem. Soc., 57, 2556 (1935)]. The intermediate amidrazone formed was evaporated on a rotary evaporator and then heated in a wood's metal bath. The residue was cooled and 500 ml of ether and 250 ml water was added; the ether layer was separated and extracted with 1N NaOH. Neutralization of the basic solution with $CO_2$ gave a white precipitate which was recrystallized from ethyl acetate. Recrystallization from benzene gave the corresponding triazolyl propanol having a melting point of 116°–117° C.

A solution of the triazolyl propanol (14 g, 0.07 mole) in 50 ml glacial acetic acid was added dropwise over a 30 minute period to a solution of 28 g (0.28 mole) of chromium trioxide in 350 ml of aqueous acetic acid (90%). The temperature was maintained at about 5° to 10° C during the addition and for a period of 2 hours. The solution was then allowed to warm to room temperature and remained at this temperature for one day. The solution was then evaporated to dryness, residue taken up on aqueous sodium bicarbonate, treated with charcoal and neutralized with dilute hydrochloric acid to give a white precipitate. Recrystallization of the precipitate from acetone produced 4 g of white crystals of the desired monohydrate, m.p. 116°–117° C.

Calcd for $C_{11}H_{11}N_3O_2.H_2O$: C, 56.16; H, 5.57; N, 17.87. Found: C, 55.58; H, 5.95; N, 18.12

Mass spectrophotometry and analysis gave a molecular weight of 217 and an empirical formula of $C_{11}H_{11}N_3O_2$.

EXAMPLE 2

3-[1-(3-chloro)-phenyl-1,2,4,(1H)-triazol-3-yl] propionic acid

A mixture of 24 g (0.1 mole) of 1-[1-(3-chloro)-phenyl-1,2,4,(1H)-triazolyl-3]propanone-2, 4 g (0.12 g-atom) of sulfur, and 10 g (0.12 mole) of morpholine were heated on a wood's metal bath at 110° C for 5 hours. When cool, the dark mass remaining in the flask was hydrolyzed directly by refluxing it for 5 hours in 100 ml of acetic acid and 100 ml of concentrated HCl. Evaporation under reduced pressure gave a residue which was taken up in aqueous sodium bicarbonate and filtered. Neutralization with dilute HCl gave a solid which was recrystallized from ethyl acetate to give 6 g of the desired triazolyl acid as white crystals, m.p. 158° C. Calcd for $C_{11}H_{10}ClN_3O_2$: C, 52.49; H, 4.05; N, 16.70. Found: C, 52.17; H, 3.75; N, 16.55

The following compound was prepared by a similar procedure, substituting 1-[1-(3,5-dichloro)-phenyl-1,2,4,-(1H)-triazolyl-3]-propanone-2 for the propanone of Example 2.

EXAMPLE 3

3-[1-(3,5-dichloro)-phenyl-1,2,4,(1H)-triazol-3yl]propionic acid

M.P. 200° C.

Calcd for $C_{11}H_9Cl_2N_3O_2$: C, 46.19; H, 3.17; N, 14.69. Found: C, 45.88; H, 3.11; N, 14.48

Examples 4 through 7 have the structure shown in Formula III wherein $R^1$ is hydrogen, $R^2$ is 2-carboxyethyl and $R^3$ is an aryl-substitutent as defined hereinbefore:

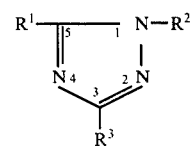

EXAMPLE 4

3-[3-phenyl-1,2,4,(1H)-triazol-1-yl]propionic acid

A twenty-nine gram portion (0.20 mole) of 3-phenyl-1,2,4,(1H)-triazole was dissolved in 150 ml of water containing 8 g (0.20 mole) of NaOH [See *J. Chem. Soc.* 3319 (1954)]. A 22 gram portion (0.20 mole) of 3-chloropropionic acid was dissolved in 150 ml of water containing 17 g (0.20 mole) of sodium bicarbonate. The two solutions were combined and refluxed for 2 days. Neutralization with dilute HCl gave a precipitate which was taken up in 500 ml of ether, extracted with aqueous sodium bicarbonate solution and neutralized. The resulting precipitate was recrystallized from isopropanol to give 9.5 g of the desired triazolyl propionic acid as off-white needles, m.p. 141° C.

Calcd for $C_{11}H_{11}N_3O_2$: C, 60.82; H, 5.11; N, 19.35. Found: C, 60.97; H, 5.03; N, 20.43.

The following compounds were prepared by a similar procedure.

EXAMPLE 5

3-[3-(3-bromo)-phenyl-1,2,4,(1H)-triazol-1-yl]propionic acid

M.P. 155° C.

Calcd for $C_{11}H_{10}BrN_3O_2$: C, 44.63; H, 3.41; N, 14.20. Found: C, 44.42; H, 3.32; N, 14.43.

EXAMPLE 6

3-[3-(3-chloro)-phenyl-1,2,4,(1H)-triazol-1-yl]propionic acid

M.P. 143° C.

Calcd for $C_{11}H_{10}ClN_3O_2$: C, 52.49; H, 4.00; N, 16.70. Found: C, 52.31; H, 3.92; N, 17.34.

EXAMPLE 7

3-[3-(4-methyl)-phenyl-1,2,4,(1H)-triazol-1-yl]propionic acid

M.P. 163° C.

Calcd for $C_{12}H_{13}N_3O_2$: C, 62.32; H, 5.66; N, 18.17. Found: C, 62.15; H, 5.56; N, 18.58.

What is claimed is:

1. 3-[3-phenyl-1,2,4,(1H)-triazol-5-yl]propionic acid monohydrate, and pharmacologically acceptable, non-toxic salts thereof.

2. A compound of the formula

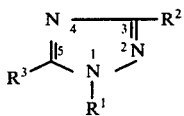

and pharmacologically acceptable, non-toxic salts thereof wherein:
- $R^1$, $R^2$ and $R^3$ are always dissimilar;
- $R^1$ is selected from the group consisting of monochlorophenyl and di-chlorophenyl;
- $R^2$ is 2-carboxyethyl; and
- $R^3$ is hydrogen.

3. A compound as claimed in claim 2, 3-[1-(3-chloro)-phenyl-1,2,4,(1H)-triazol-3-yl]propionic acid.

4. A compound as claimed in claim 2, 3-[1-(3,5,-dichloro)-phenyl-1,2,4,(1H)-triazol-3-yl]propionic acid.

5. A compound of the formula

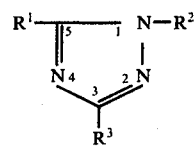

and pharmacologically acceptable, non-toxic salts thereof wherein:
- $R^1$, $R^2$ and $R^3$ are always dissimilar;
- $R^1$ is hydrogen;
- $R^2$ is 2-carboxyethyl; and
- $R^3$ is selected from the group consisting of phenyl, 4-methylphenyl, mono-bromophenyl and mono-chlorophenyl.

6. A compound as claimed in claim 5, 3-[3-phenyl-1,2,4,-(1H)-triazol-1-yl]propionic acid.

7. A compound as claimed in claim 5, 3-[3-(3-bromo)-phenyl-1,2,4,(1H)-triazol-1-yl]propionic acid.

8. A compound as claimed in claim 5, 3-[3-(3-chloro)-phenyl-1,2,4,(1H)-triazol-1-yl]propionic acid.

9. A compound as claimed in claim 5, 3-[3-(4-methyl)-phenyl-1,2,4,-(1H)-triazol-1-yl]propionic acid.

10. A therapeutic method for treating algia in an individual for whom such therapy is indicated, comprising: administering to the individual an effective analgesic amount of 3-[3-phenyl-1,2,4,-(1H)-triazol-5-yl]propionic acid monohydrate and pharmacologically acceptable, nontoxic salts thereof.

11. A therapeutic method for treating algia in an individual for whom such therapy is indicated, comprising:
administering to the individual an effective analgesic amount of a compound of the formula

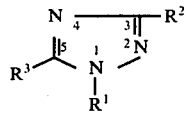

and pharmacologically acceptable, non-toxic salts thereof wherein:
- $R^1$, $R^2$ and $R^3$ are always dissimilar;
- $R^1$ is selected from the group consisting of monochlorophenyl and di-chlorophenyl;
- $R^2$ is 2-carboxyethyl; and
- $R^3$ is hydrogen.

12. A therapeutic method for treating algia in an individual for whom such therapy is indicated, comprising:
administering to the individual an effective analgesic amount of a compound of the formula

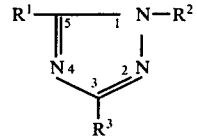

and pharmacologically acceptable, non-toxic salts thereof wherein:
- $R^1$, $R^2$ and $R^3$ are always dissimilar;
- $R^1$ is hydrogen
- $R^2$ is 2-carboxyethyl; and
- $R^3$ is selected from the group consisting of phenyl, 4-methylphenyl, mono-bromophenyl and mono-chlorophenyl.

* * * * *